United States Patent [19]
Lawrence et al.

[11] Patent Number: 5,691,466
[45] Date of Patent: Nov. 25, 1997

[54] LIQUID-SENSING APPARATUS AND METHOD

[75] Inventors: John Michael Walmsley Lawrence; John Frederick Harkness, both of Newbury, Great Britain

[73] Assignee: J.T.L. Systems Ltd., Great Britain

[21] Appl. No.: 673,723

[22] Filed: Jun. 26, 1996

[30] Foreign Application Priority Data

Jun. 28, 1995 [GB] United Kingdom ............ 9513191
Dec. 14, 1995 [GB] United Kingdom ............ 9525488

[51] Int. Cl.⁶ .................................... G01N 25/56
[52] U.S. Cl. .................... 73/29.05; 374/148; 62/129
[58] Field of Search ................. 73/29.01, 29.05, 73/861.04, 204.12, 204.19, 204.22, 204.23; 62/125, 126, 129; 374/147, 148

[56] References Cited

U.S. PATENT DOCUMENTS

| | | | |
|---|---|---|---|
| 2,400,334 | 5/1946 | Berry | 62/4 |
| 2,577,902 | 12/1951 | McGrath | 62/8 |
| 3,068,693 | 12/1962 | Ferran et al. | 73/204.19 |
| 3,366,942 | 1/1968 | Deane | 340/243 |
| 3,735,603 | 5/1973 | Hamilton | 62/210 |
| 3,898,638 | 8/1975 | Deane et al. | 340/243 |
| 4,167,858 | 9/1979 | Kojima et al. | 62/126 |
| 4,311,047 | 1/1982 | Hubbard, Jr. et al. | 73/204.19 X |
| 5,044,764 | 9/1991 | Aoki et al. | 374/16 |

FOREIGN PATENT DOCUMENTS

| | | |
|---|---|---|
| A155826 | 9/1985 | European Pat. Off. |
| 210509 | 7/1986 | European Pat. Off. |
| 485185 | 5/1992 | European Pat. Off. |
| 1055018 | 4/1959 | Germany |
| 3818584 | 12/1989 | Germany |
| 620951 | 4/1949 | United Kingdom |
| 1480349 | 7/1977 | United Kingdom |
| 1506999 | 4/1978 | United Kingdom |
| 2008799 | 6/1979 | United Kingdom |
| 2143950 | 2/1985 | United Kingdom |
| 2157447 | 10/1985 | United Kingdom |
| 2181257 | 4/1987 | United Kingdom |

OTHER PUBLICATIONS

Patent Abstracts of Japan, vol. 14, No. 481 (M-1037), Oct. 19, 1990 & JP-A-02 195164 (Sugimoto Takeshi), Aug. 1, 1990.

*Primary Examiner*—Michael Brock
*Attorney, Agent, or Firm*—Andrus, Sceales, Starke & Sawall

[57] ABSTRACT

A device for detecting the presence of liquid in a flow of gas has a heated temperature sensor mounted on a heated member in thermal contact with the gas and an unheated temperature sensor in thermal contact with the gas, but thermally isolated from the heated temperature sensor. Liquid in the gas flow evaporates by absorbing heat from the heated member and therefore reduces the temperature of the heated temperature sensor. The reduction in temperature is used to detect the presence of liquid. The device is suitable for detecting liquid at the output of an evaporator in a heat transfer system, and may be used as part of a control system which reduces the flow of refrigerant through the evaporator when liquid is detected at the output, so avoiding damage caused by liquid entering the compressor of the heat transfer system.

40 Claims, 4 Drawing Sheets

LIQUID-SENSING APPARATUS AND METHOD

FIELD OF THE INVENTION

This invention relates to a liquid-sensing apparatus suitable in particular, although not exclusively, for detecting a liquid component in the fluid output of an evaporator of a heat transfer system. The invention also relates to heat transfer system incorporating such a liquid-sensing apparatus and to a method of detecting a liquid component in a predominantly gaseous fluid.

BACKGROUND OF THE INVENTION

One example of a heat transfer system is a commercial refrigeration system, as shown schematically in FIG. 1.

Commercial refrigeration systems use the vapour compression cycle, in which the removal of heat relies on evaporation. A liquid refrigerant turns into gas in an evaporator 1, and in the process of doing so absorbs heat. The gas turns back into liquid in a condenser 2, and in the process of doing so releases heat in a location removed from that of the evaporator 1. The refrigerant fluid is pumped around a circuit connecting the evaporator and the condenser by a motor-driven pump or compressor 3. An expansion valve 4 serves to control or meter the rate at which the liquid refrigerant enters the evaporator. The system has a low pressure side LP and a high pressure side HP. The gas coming out of the evaporator 1 and entering the compressor 3 is at a relatively low pressure, whereas the gas coming out of the compressor 3 and entering the condenser 2 is at a relatively high pressure. The liquid coming out of the condenser 2 is at the same high pressure. Thus, a pressure difference exists across the compressor 3 and also across the expansion valve 4.

The efficiency of the system is dependent upon the amount of work done by the compressor 3, which itself is related to the size of the pressure difference between the high pressure side HP and the low pressure side LP of the system. In order to optimize the efficiency, the condensing pressure should be as low as possible and the evaporating pressure should be as high as possible. This is because the smaller the pressure difference across the compressor 3, the greater is the amount of fluid pumped by the compressor 3 per unit time. Thus, the difference in pressure between the high pressure side HP and the low pressure side LP of the system should be minimized.

For effective use of the evaporator 1, the proportion of the total length of the evaporator pipe in which the liquid is present so that evaporation can occur should be as large as possible. However, the refrigerant at the outlet normally needs to be kept totally gaseous, since if liquid or mist enters the compressor 3, damage is likely to result. The amount by which the fluid output of the evaporator 1 is hotter than necessary to be gaseous is known as the superheat. This can be defined as the temperature of the gas at the evaporator outlet minus the saturated vapour temperature corresponding to the gas pressure at the outlet. In other words, the superheat is the amount by which the temperature of the gas exceeds the boiling point of the liquid at the particular pressure.

Ideally, the superheat should be maintained at practically zero degrees, but normally it is controlled within a small range of values having a predetermined minimum level a few degrees above zero. The superheat is controlled by means of the expansion valve at the evaporator inlet. If there is no superheat, the rate of liquid flow into the evaporator should be reduced. If there is too much superheat, the rate can be increased.

For the type of commercial refrigeration cabinets found in supermarkets and other stores, a thermostatic expansion valve has been traditionally used as the control device at the inlet of the evaporator. One significant disadvantage of using a thermostatic expansion valve is that the operation of the valve relies on the pressure of the liquid from the condenser. Thus, for this type of expansion valve to work a relatively high pressure difference across the valve is required. This makes greater the amount of work that needs to be done by the compressor, thereby reducing the efficiency.

More recently, it has been proposed to replace the traditional thermostatic expansion valve with an electrically-controlled one. The use of such an electrically-actuated expansion valve has a number of attractions. Perhaps the greatest is the potential for energy saving. As compared with the thermostatic version, the electric expansion valve requires only a small pressure drop across it to operate. This means that a lower condensing pressure and temperature can be adopted, enabling the compressor to pump a greater quantity of refrigerant per unit of electricity used, and thereby operate more efficiently.

Despite this potential benefit, refrigeration systems incorporating electronic control of the refrigerant flow have gained only a limited share of the market to date. One of the key reasons is that many of the proposed designs cannot satisfactorily detect an absence of superheat, and are therefore prone to malfunction or failure due to the resultant flooding and damage of the compressor.

Accordingly, there is a need for a liquid-sensing apparatus capable of reliably and speedily detecting the onset of liquid in a fluid which is normally in the gas state. Needless to say, such a liquid-sensing apparatus will find useful application in a wide variety of situations other than that specifically described above by way of illustration, in which maintaining a gaseous environment is important.

The document GB-A-2 157 447 discloses a measuring device for heat exchange equipment, in which the presence of a liquid component in a refrigerant leaving an evaporator is detected by means of a heating element and two temperature sensors disposed on the outside wall of a suction conduit, with one of the temperature sensors positioned close to and the other spaced away from the heating element. The difference in temperature between the two sensors is used to detect the presence of liquid in the refrigerant. This measuring device relies on the difference in thermal transfer coefficient between wet and dry refrigerant. The optimum spacing between the heating element and the temperature sensors for detecting this difference depends on the geometry of the suction conduit. Hence, installation of such a device is complicated. If the device is integrated in a common housing, then the device can only be used with equipment having a suction conduit of the size for which the device was designed.

SUMMARY OF THE INVENTION

According to one aspect, the present invention provides a liquid-sensing apparatus for sensing liquid in a flow of fluid which is predominantly gaseous, the apparatus comprising a first temperature sensor and a heating means mounted on a first member in thermal contact with the fluid and with each other, a second temperature sensor mounted in thermal contact with the fluid, and means for thermally isolating the first member from surrounding thermally conductive portions. According to another aspect of the invention, there is provided a method of using such a liquid-sensing apparatus, in which the presence of liquid is determined by detecting a drop in temperature of the first temperature sensor due to the latent heat of the liquid evaporating when heated by the heating means. According to another aspect of the invention, there is provided a control apparatus for a heat transfer system including the liquid sensing apparatus. The present invention extends to a heat transfer system incorporating such control apparatus.

According to an embodiment of the invention, the presence of liquid in the fluid is detected using the two temperature sensors. One of the temperature sensors is deliberately heated above the surrounding gas temperature, while the other temperature sensor serves to provide a reference measurement. A difference in the temperatures sensed by the two temperature sensors is monitored. When liquid appears in the fluid and makes contact with the heating means, the heat supplied by the heating means is consumed as the latent heat of evaporation in converting the liquid to gas, thus causing a detectable fall in the monitored temperature difference between the two sensors. The provision of means for thermally isolating the two sensors ensures that a fast and reliable response to the detection of liquid is achieved.

In a preferred application, the apparatus is connected to the outlet of an evaporator in a heat exchange system such as refrigeration or air conditioning equipment. For example, the apparatus may be connected to the suction pipe connecting the evaporator output to a compressor. This arrangement offers a simple, yet highly effective way of preventing a wet fluid output from damaging the compressor. Moreover, the size of the temperature change is dependent on the amount of liquid. This provides the advantage of being able to determine not just the absence of superheat in the fluid output but also its degree of wetness. A small amount of liquid at the evaporator outlet may be tolerable by virtue of the length of the suction pipe, and is advantageous in ensuring that liquid is present throughout the length of the evaporator and therefore the whole of the evaporator is effective in absorbing heat. Thus, a threshold may be set for taking action when the amount of liquid exceeds the tolerable or a desirable upper limit.

In a preferred embodiment of the invention, the heating means and the first temperature sensor are mounted on a first portion of the wall of a tube through which, in use, the fluid flows and the second temperature is mounted on a second portion of the tube wall, and at least one of the two tube wall portions is thermally isolated from the main portion of the tube by means of a surrounding one or more apertures, preferably in the form of elongate slots. The two tube wall portions may be disposed adjacent each other with one or more apertures or slots providing thermal isolation therebetween. Alternatively, the two portions are disposed on opposing sides of the tube, for example in diametrically opposing positions on a circular pipe. In each case, all of the apertures or slots are sealed so as to maintain the fluid-tight environment of the tube. The elongate slots may extend entirely around one or both of the tube wall portions, in which case the sealing means completely supports the portion or portions. The sealing means is suitably a plastic moulding which surrounds the pipe.

Thermally isolating the heated wall portion is especially advantageous in removing any heat-sinking effect of the surrounding wall. This means that a small, low power heating resistor, for example 1 W, may be used. Moreover, the speed of response in liquid detection and of recovery thereafter becomes higher.

In a preferred arrangement, one or both of the sensor portions is arranged to project inwardly of the tube. More preferably, the or each portion is inclined with respect to the longitudinal axis of the tube so as to face the oncoming fluid flow. These arrangements further improve the speed and effectiveness of the response, although they are not essential to achieving the object of the invention.

In alternative embodiments, the first temperature sensor and the heating means are mounted in a housing which projects from the wall of a tube into the fluid flow, such that the housing protects the sensors from the fluid. In one alternative embodiment, the second temperature sensor is mounted in a housing separate from that of the first temperature sensor, the housings being mounted separately on the tube wall and thermally insulated from each other, for example by forming a part of the tube wall of thermally insulating material.

In another alternative embodiment, the first temperature sensor and the heating means are mounted on a first housing portion, the second temperature sensor is mounted on a second housing portion, and the first and second housing portions are assembled with a thermally insulating portion disposed between them, so as to form a housing which seals the temperature sensors and heating means from the fluid flow. The second housing portion is in thermal contact with the tube wall, while the first housing portion is thermally insulated from the tube wall by means of the thermally insulating portion.

BRIEF DESCRIPTION OF THE DRAWINGS

The invention is more fully explained and illustrated, although not limited, by the following description with reference to the accompanying drawings, in which:

FIGS. 3 to 5 are schematic, simplified views of a liquid-sensing apparatus according to a first embodiment of the invention, in which FIG. 4 is a plan view, FIG. 3 is a sectional view on line A—A of FIG. 4 and FIG. 5 is a sectional view on line B—B of FIG. 3;

FIGS. 7 to 9 are schematic, simplified views of a liquid-sensing apparatus according to a second embodiment of the invention, in which FIG. 8 is a plan view, FIG. 7 is a sectional view on line C—C of FIG. 8 and FIG. 9 is a sectional view on line D—D of FIG. 7;

FIGS. 10 and 11 are schematic simplified drawings of a liquid-sensing apparatus according to a third embodiment of the invention, in which FIG. 10 is a side sectional view and FIG. 11 is a transverse sectional view on line E—E of FIG. 10.

DETAILED DESCRIPTION OF THE PREFERRED EMBODIMENTS

Figure 1:
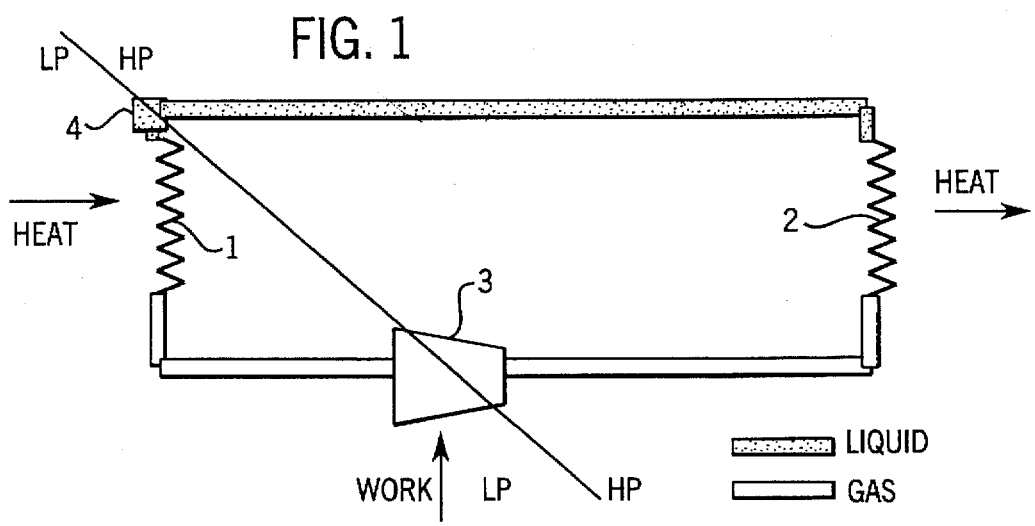
FIG. 1 is a schematic drawing of a refrigeration system.
Figure 2:
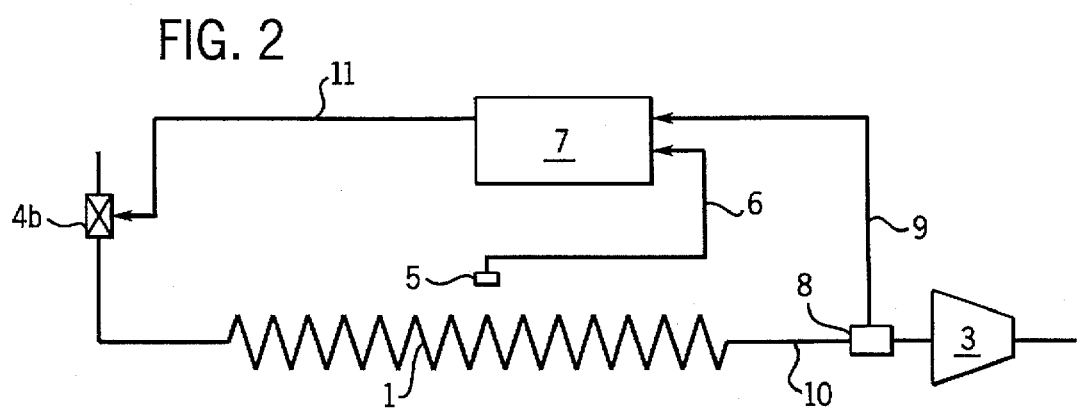
FIG. 2 is a schematic drawing of part of a refrigeration system including liquid sensing apparatus in accordance with the present invention.

Referring to FIG. 2, a refrigeration system and sensor device according to an embodiment of the invention will be described. The refrigeration system represents one example of a heat transfer system. The system has the basic configuration shown in FIG. 1 (the part of the circuit including the condenser 2 with which this invention is not concerned, being omitted in FIG. 2), and takes the form of a refrigeration cabinet for storing food or drinks at a predetermined temperature or within a predetermined range of temperatures. Here, the medium to be cooled using the evaporator 1 is the air which flows over the evaporator and circulates around the products. In order to monitor and control the refrigeration operation, one or more temperature sensors 5 is arranged to sense the air temperature in the vicinity of the evaporator and an estimated product temperature is calculated therefrom in a manner known to those skilled in the art. The temperature sensor 5 may measure one of the "air on" and the "air off" temperatures, that is the temperature of air circulating towards and of air leaving the evaporator, respectively, and supply the measurement as a signal on line 6. The product temperature is calculated as a function of the measured temperature, or both temperatures if two sensors are employed. The calculated product temperature constitutes one control input used by a control circuit 7.

A second control input used by the control circuit 7 is derived from the output of a sensor device 8 on line 9. If two temperature sensors are used in the sensor device 8, the second control input may comprise two separate inputs from the respective sensors. The sensor device 8 is arranged at the outlet of the evaporator 1 and detects the presence of any liquid in the normally gaseous output fluid. The sensor device 8 is suitably mounted in the suction pipe 10 connecting the evaporator to the compressor 3, and the pipe 10 may be expanded or include an expanded vessel to receive the device for this purpose. However, the location of the sensor device is not especially critical, provided it comes into contact with the fluid flow; references herein to the outlet of the evaporator should be interpreted accordingly.

The flow of liquid refrigerant into the evaporator is controlled by an electrically-actuated expansion valve 4b. The valve 4b comprises the valve mechanism itself and an actuator for controlling the state of the valve. The actuator receives an electrical control signal on line 11 from the control circuit 7. The signal takes the form of a periodic pulse whose duration is varied to adjust the flow rate. For the length of the pulse the actuator holds the valve open, otherwise the valve is closed. Thus, the flow rate is determined by the mark/space ratio of the pulse within the periodic cycle. This ratio is set according to the control input(s) to the circuit 7.

Before describing in detail the sensor device 8, an explanation of one example of a control regime will be given. The first control input derived from the temperature sensor(s) 5 is the basic control input. In basic operation, the control circuit 7 will set the mark/space ratio of the signal on line 11, determining the opening/closing time of the valve 4b, according to how the calculated product temperature relates to a desired temperature or range of temperature preset or programmed in the circuit 7. Thus, the system operates continuously (excepting any defrost) with a variable amount of superheat, higher if the product is adequately cool or lower if further cooling is required. The second control input, indicating the detection of liquid in the fluid coming out of the evaporator 1, overrides the basic control according to the first control input by causing the input refrigerant flow to be reduced or, if necessary, interrupted irrespective of the demand determined by the first control input. The control according to the first control input may be resumed as soon as the second control input has ceased, or a predetermined delay thereafter which ensures full recovery and thereby more stable operation. Therefore, it can be seen that this system is highly responsive to any change in the load condition, uses a preferred continuous flow of fluid, and prevents damage to the compressor by immediately reacting to the fluid output of the evaporator becoming wet. It also offers the potential significant energy savings associated with using an electric expansion valve.

Figure 4:
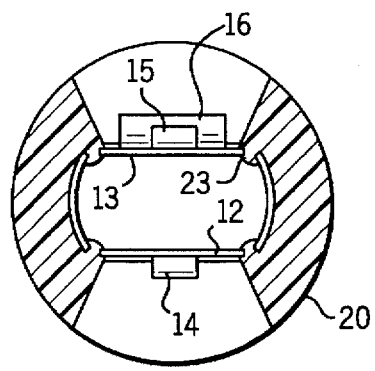
Figure 5:
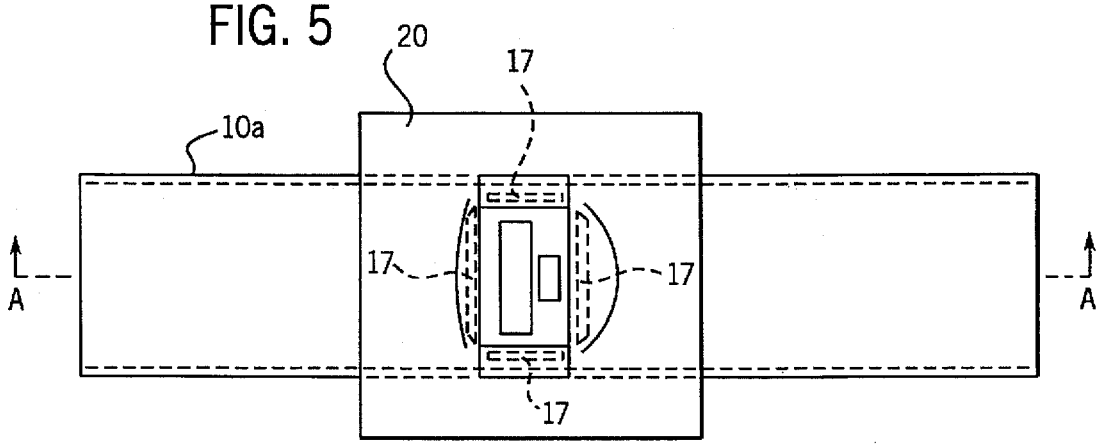

The sensor device 8 in a first embodiment will now be described with reference to FIGS. 3 to 5.

The apparatus comprises principally a tube 10a and a number of components 14 to 16 mounted on the tube, externally thereof. The components consist of a first temperature sensor 15, an electrical heating element 16 mounted adjacent the sensor 15, and a second temperature sensor 14. In this embodiment the two temperature sensors 14, 15 are each temperature-dependent resistors or thermistors, whereas the heating element 16 is an electrical resistor. The thermistor 15 and heating resistor 16 are mounted side-by-side on a first portion or member 13 of the tube wall. The other thermistor 14 is mounted on a second portion or member 12 of the tube wall, diametrically opposing the first portion. The tube 10a is made of a material having a good thermal conductivity, preferably a metal or metal alloy. In this embodiment a copper tube is used.

Figure 3:
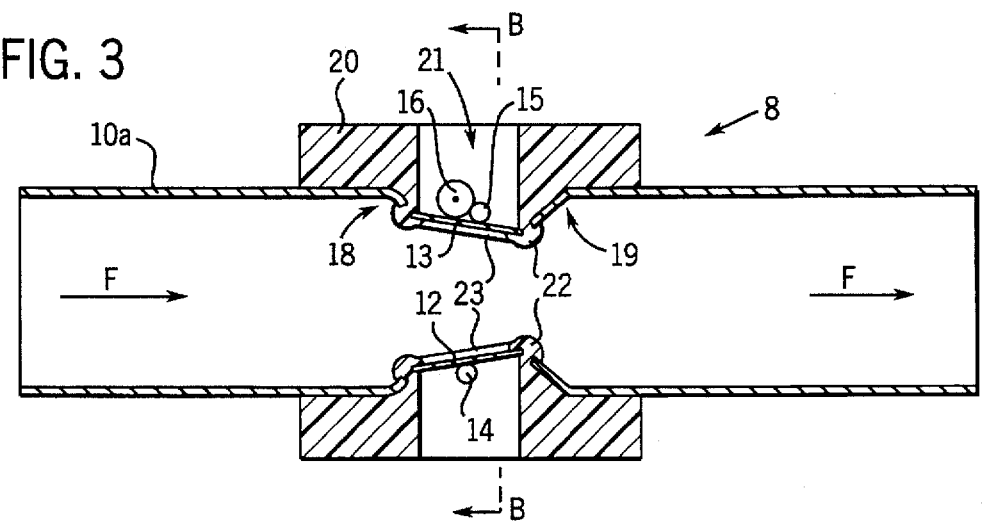

In operation, a fluid which is normally in the gas state flows through the tube 10a in a direction indicated generally by the arrows F in FIG. 3. Both of the thermistors 14, 15 are responsive to the temperature of the fluid flowing past the members 12, 13. In a wholly gaseous fluid, the member 12 will acquire substantially the gas temperature and this temperature is sensed by the thermistor 14. On the other hand, the member 13 will acquire a temperature higher than the gas temperature due to the heating effect of the resistor 16, and this higher temperature is sensed by the thermistor 15.

Thus, when the fluid is gas only and contains no liquid component, there will exist a definite temperature difference between the temperatures sensed by the sensors 14, 15, the difference being determined practically by the magnitude of the current supplied to the heating resistor 16. The difference between the two sensed temperatures is of the order of a few degrees Celsius. In this embodiment, the temperature difference is monitored by a detection means comprising a comparator (not shown). The comparator may be incorporated in the apparatus itself, but it is conveniently provided in external circuitry. The detection means is readily implemented using electronic components with which the skilled person is familiar.

When liquid appears in the fluid flowing through the tube, the liquid comes into contact with the heated wall portion 13 of a temperature exceeding that of the fluid. The effect of this contact is that the liquid immediately vaporises, the heated portion 13 providing the necessary latent heat for the change of state. The vaporisation of the liquid is manifest by a rapid or sudden lowering of the temperature of the portion 13, which is detected by the thermistor 15. Thus, by monitoring the difference between the temperatures sensed by the thermistors 14 and 15, the occurrence of liquid in the fluid flow can be quickly and reliably established by detecting the corresponding lowering of the temperature difference. For example, the detection may be achieved by setting a threshold for the output of the comparator: if the output level, corresponding to the temperature difference, falls below the threshold (for example, instantaneously or for a predetermined period), an output signal indicating liquid detection is generated.

The size of the temperature difference is dependent on the amount of liquid, i.e. the ratio of liquid to gas in the fluid being monitored. Thus, it is possible to set the threshold for detection at a level which corresponds to a particular degree of wetness which needs to be checked. This is an advantageous development.

In accordance with a feature of this invention, the two portions 12, 13 of the tube wall on which the sensing components 14 to 16 are mounted, are substantially thermally isolated from each other. That is to say the apparatus includes means deliberately provided for substantially hindering the transmission of heat from the heated portion to the unheated portion, of the tube wall. The manner in which this thermal isolation is achieved in the present embodiment will now be described.

Figure 6:
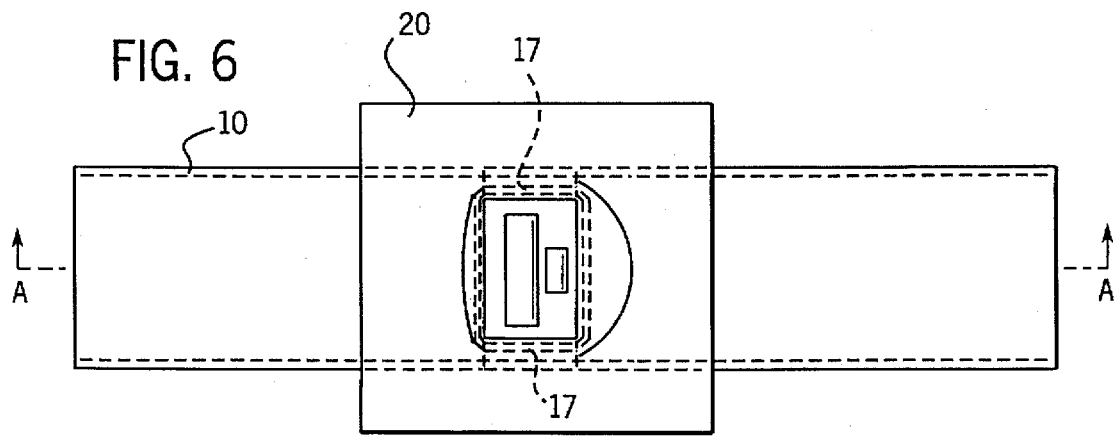
FIG. 6 shows a plan view of an alternative first embodiment.

Each of the sensor-mounting portions 12, 13 consist of a generally rectangular portion of the tube wall which is isolated from the rest of the tube by a surrounding plurality of apertures in the tube wall, here in the form of four elongate slots 17. These slots 17 are best seen in FIG. 5 in respect of the heated wall portion 13. The unheated wall portion 12 is similarly formed. This arrangement results in the portion 12, 13 being attached to the remainder of the tube merely at its corners in a structure which resembles a web. The form or shape, number and extent of the apertures or slots may be varied in many ways. Indeed, there may even be just one slot, for example extending around three sides of the sensor portion in a substantially U-shaped configuration. In an alternative, the slot 17 extends completely around the sensor portion so that the sensor portion is a separate piece from the tube 10a, as shown in FIG. 6. The overall amount of the tube wall which is removed naturally determines the degree of thermal isolation of the sensor portion.

In this embodiment, in addition to having the isolating slots 17, the two sensor portions 12, 13 are arranged so as to project into the body of the tube, as seen in FIG. 3. This projection is done by forming two bends 18, 19 in the tube, before and after each sensor portion as seen in the general fluid flow direction F.

Preferably, the second bend 19 is made deeper than the first bend 18, whereby the sensor portion is inclined toward the oncoming fluid flow (to the left in FIG. 3). This will improve the detection sensitivity, although the same effect may be achieved by creating some turbulence in the fluid flow adjacent the sensor portion.

The above-described structure of the tube 10a is conveniently realised by first punching the slots 17, and then performing a pressing operation to form the bends 18, 19. A ductile material such as copper for the tube wall makes these operations practical.

In order to maintain the tube fluid-tight, the apertures must all be carefully sealed by means of a suitable sealant. The choice of material for the sealant will depend on a number of factors, including the range of operating pressure, the chemical nature of the fluid and the material of the tube itself. In this embodiment, the slots 17 are sealed by means of a moulding of plastics material, which is moulded in situ so as to surround the pipe. The moulding material, for example nylon, is injected externally through the slots 17 and sets to form sealing lips 22, 23 internally of the pipe.

In the alternative shown in FIG. 6 in which the slot 17 extends completely around the sensor portion, the sensor portion is held in position while the moulding material is injected, with the means for holding the sensor portion in position being removed once the moulding material has set. The moulding material then serves to hold the sensor portion in position.

The moulding 20 has a secondary function of strengthening the pipe, which is inevitably weakened by the presence of the slots 17 and the bends 18, 19. Thus, the pipe is strengthened, the sensor portions supported and the slots 17 sealed, all by means of the moulding 20. Additionally, the moulding 20 includes cavities 21 in which the sensor portions of the tube wall are exposed for mounting of the components 14 to 16. Once these components have been fitted, the cavities 21 may be filled with potting compound and set, the wiring to the components (not shown) being extracted through the potting compound at the opening of the cavity 21. Before the cavity is potted, the components and the wall portions should be coated with heat-sinking compound to improve the thermal transmission performance.

Figure 7:
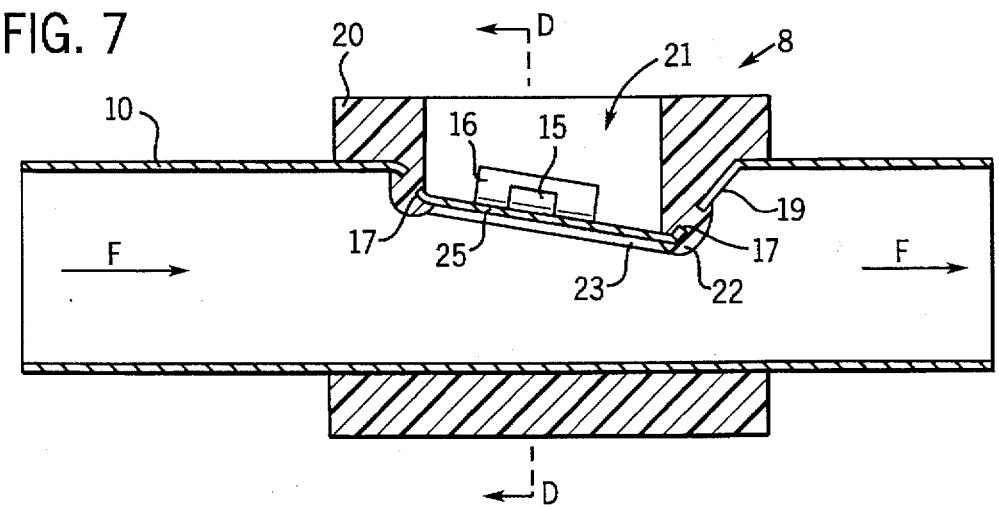

The sensor device 8 in a second embodiment of the invention will now be described with reference to FIGS. 7 to 9. In these drawings, like reference numerals denote parts which are the same as or corresponding to those of the first embodiment. Such components will not be described again in detail.

The second embodiment differs principally from the first embodiment in that the two wall portions 25, 27 on which the sensor components are mounted are arranged side-by-side, as compared with the opposing wall portions 12, 13 of the first embodiment. This simplifies the fabrication in terms of the structures of the pipe 10 and the moulding 20, and in that the wiring to the three components 14 to 16 may be extracted at a single location. As in the first embodiment, each sensor portion 25, 27 is bounded by one or more elongate slots 17. However, in this embodiment, the two portions share a common dividing slot 26 extending generally in the fluid flow direction. Again, the arrangement of the slots may be varied in many ways. However, it is preferable that the one or more slots 26 which separate the two sensor portions 25, 27 cover substantially the full length of the portions, in view of their mutual proximity. Additionally, the moulding 22 may include a partitioning wall 24 within the cavity 21, the low thermal conductivity of the moulding improving the thermal isolation.

Figure 8:
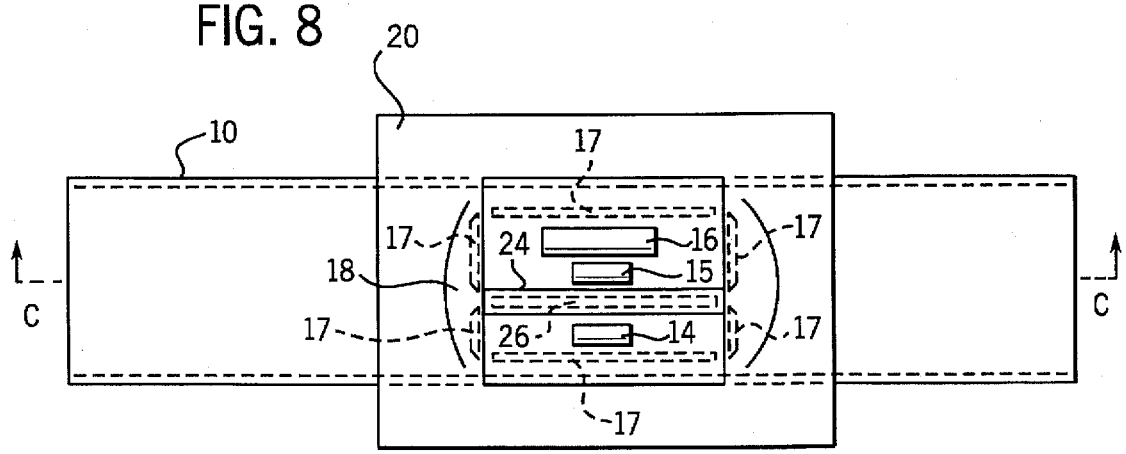
Figure 9:
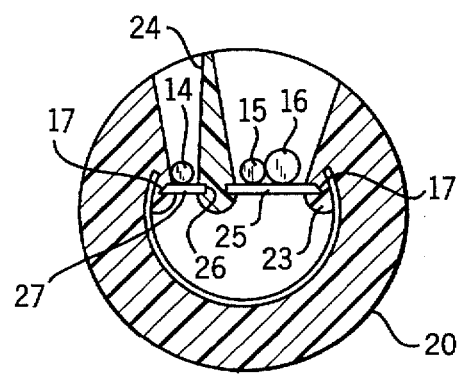

In the second embodiment, as seen in FIG. 8, the two sensor portions 25, 27 of the tube wall are separated by a slot 26 extending in the direction of the tube axis. Although this is a preferred arrangement, the two portions 25, 27 may alternatively be separated by a dividing slot or slots extending in another direction such as transverse the tube, in which case the sensor components 14 to 16 may be mounted in the orientation shown in the first embodiment.

In the above-described embodiments, each of the wall portions 12, 13, 25, 27 is arranged so as to project into the body of the tube 10a, and moreover is inclined so as to face the incoming fluid flow. However, although preferred, none of these features is essential, since mutually isolated portions of the basic tube wall would still be disposed in and responsive to the passing fluid flow. Furthermore, it is possible to omit the slots 17 which isolate the portion 12 or 27 having the unheated sensor 14. The isolation of the heated portion 13 or 25 is the more significant, since it serves to alleviate the local heat-sinking effect of the surrounding tube, thereby allowing the use of a lower power heating resistor 16 and ensuring the availability of heat for rapid supply of the latent heat of evaporation when liquid contacts the heated portion. In the case of the second embodiment, if the surrounding slots 17 are omitted, the one or more slots 26 which thermally isolate the unheated portion 27 from the heated portion 25 should be maintained.

Figure 10:
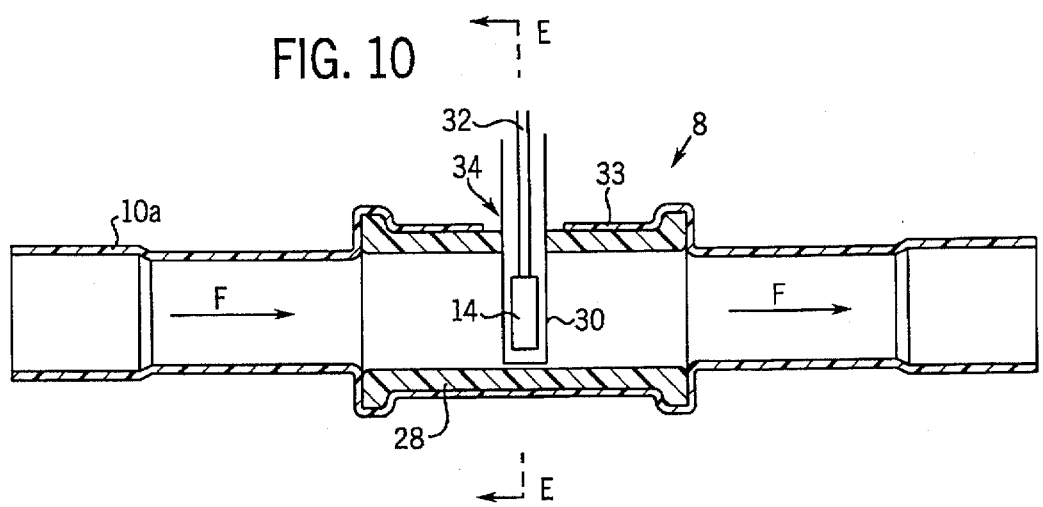
Figure 11:
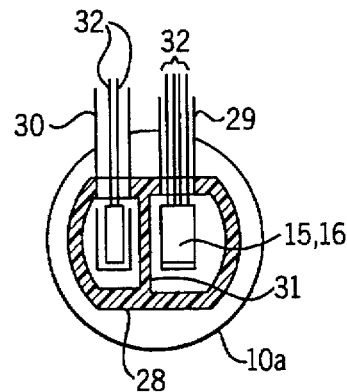

FIGS. 10 and 11 illustrate the sensor device 8 in a third embodiment of the invention. In these drawings, like reference numerals denote parts which are the same as or corresponding to those of the first and second embodiments. Such components will not be described again in detail.

This embodiment differs from the previous two embodiments in that the sensing components 14 to 16 are mounted inside the pipe 10 so as to be disposed in the fluid flow F. Specifically, the thermistor 15 and resistor 16 are housed together in a first cylindrical housing 29 and the thermistor 14 is housed in a second cylindrical housing 30. The two members 29, 30 should be made of a material offering good thermal conductivity. In this embodiment, the housings, like the tube 10, are made of copper.

The cylindrical housings 29, 30 extend into the tube 10 through a hole 34 in the tube wall, thereby enabling the lead wirings 32 to be extracted. In order to thermally isolate the two cylinders from the pipe wall, the cylinders are mounted in a moulding 28 of plastics material, for example nylon, contained within the pipe. The moulding provides respective holes for the entry of the cylinders, the surrounding aperture 34 in the pipe wall being larger so as to avoid thermal contact between each cylinder and the wall. The structure is potted or sealed at the entrance in order to maintain the pipe fluid-tight. The moulding 28 contains an optional partitioning wall 31 between the cylinders 29, 30 for improving the thermal isolation. The thermal contact between each cylinder and the sensing component(s) housed therein is enhanced by the application of heat-sinking compound.

The moulding 28 may be inserted longitudinally into the pipe 10 in fabrication of the apparatus. Preferably, however, the pipe is formed in situ around the moulding 28, suitably by a spinning process. This makes for a greater pressure tolerance of the final structure, which is advantageous in a refrigeration application. The moulding 28 may be flat-walled at the top or bottom as shown in FIG. 11, in which case the pipe 10 has a similar conforming flat section 33 (FIG. 10).

The operation of the apparatus is the same as for the first and second embodiments. The cylinder 29 acquires a higher temperature than the cylinder 30 by virtue of the heating resistor 16. The thermal isolation of the heated cylinder 29 from the pipe wall provides for quick evaporation of liquid upon its arrival, and thus a good speed of response. The thermal isolation of the unheated cylinder 30 from the pipe wall is less important, as in the earlier embodiments. Thus, if desired, the unheated cylinder 30 may be in thermal contact with the pipe 10.

Figure 12:
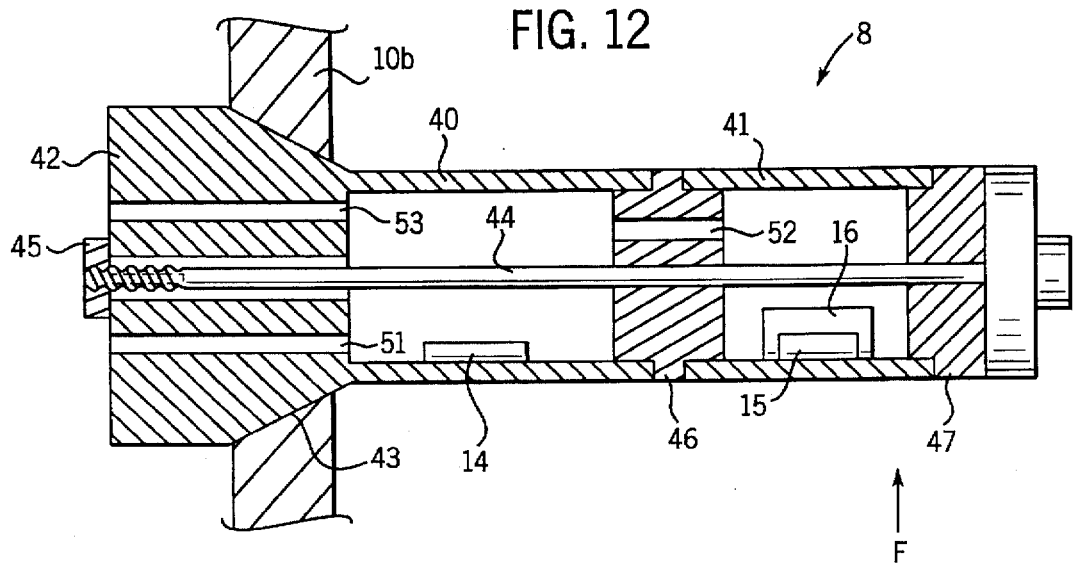
FIG. 12 is a cross-sectional view of liquid sensing apparatus according to a fourth embodiment of the invention.

The sensor device 8 in a fourth embodiment will now be described with reference to FIG. 12. The device comprises a body consisting principally of two thermally-conductive members 40, 41 in the form of hollow cylindrical housings mounted end-to-end. The member 40 includes at one end a tapered cylindrical block threaded at the surface 43 so as to permit the device to be mounted in a fluid-sealing manner in the wall 10b of the suction pipe 10 (FIG. 2) or of a vessel provided in that pipe. The two housings 40, 41 are held together by means of a bolt 44 which extends through the housings, including an axial hole in the block 42, and a nut 45 secured on a threaded end of the bolt which emerges from the hole in the block. The housings are thermally isolated from each other, both directly and via the bolt, by thermally-insulative elements in the form of washers 46, 47. The washer 46 is sandwiched between the two housings, whereas the washer 47 is sandwiched between the housing 41 and the bolt head. Each washer constitutes a thermal barrier which ensures that the temperature of each housing remains largely independent of that of the other housing.

The second temperature sensor 14 is mounted on the inside of the housing 40 in good thermal contact therewith. The sensor 14 takes the form of a temperature-dependent resistor, specifically in this embodiment a thermistor. The output lead of the thermistor (not shown) is routed externally of the device via an axial hole 51 in the block 42. The first temperature sensor 15 is similarly mounted in the housing 41, where additionally the electrical heating element 16, specifically in this embodiment an electrical resistor, is mounted adjacent the sensor 15. The sensor 15 and the heating element 16 are arranged such that the element 16 raises the temperature of the housing 41, and the sensor 15 is responsive to the temperature of the housing 41. It is preferable although not essential that the two components 15, 16 are mounted adjacent each other. The wiring (not shown) to the sensor 15 and the element 16 is routed externally of the device via axial holes 52 and 53 in the washer 46 and the block 42, respectively. The heater is powered continuously. In a prototype sensor, a heater power of 2.5 W was used. However, a lower power is likely to be suitable in practice.

The internal cavity of the body is sealed from the fluid flow and contains air at the ambient, atmospheric pressure existing outside the suction pipe 10. Thus, the electrical components 14, 15, 16 mounted in the cavity do not require special protection. The materials of the housings 40, 41, the washers 46, 47 and the bolt 44, on the other hand, must be able to survive for a reasonable period of service the physical (temperature, pressure) and chemical environment of the refrigerant fluid flow. For this purpose the housings and bolt are suitably metallic, for example brass in the case of an HFC refrigerant or stainless steel for one such as ammonia. The optimum material to be selected for the washers will also depend, to some extent, on the chemical composition of the particular refrigerant being used, but it is likely to be a thermoplastic and/or polymer.

The operation of the sensor device 8 in this embodiment is described in the following. Both of the temperature sensors 14, 15 are responsive to the temperature of the fluid flowing past the device. In a wholly gaseous fluid, the member 40 will acquire substantially the gas temperature and this temperature is sensed by the sensor 14. The member 41 will acquire a temperature higher than the gas temperature due to the heating effect of the heating element 16, and this higher temperature is sensed by the sensor 49. Since the washer 46 provides a thermal barrier between the members 40, 41 and a gas is a poor conductor of heat, the higher temperature of the member 41 will not cause the member 40 to be heated significantly above the gas temperature. This is further ensured in this embodiment by virtue of the relative dispositions of the members 40, 41 with respect to the dominant direction F of the fluid flow.

The above embodiments utilize the difference between the temperatures sensed by two temperature sensors, the heating means associated with one of the sensors. However, it will be appreciated that the principle on which the liquid-detection operation is based relies essentially on the fall in the temperature detected by the heated sensor. Thus, the unheated sensor 14 may be dispensed with in a modification of the above embodiments. In this case, the wall portion, housing or member on which the heated sensor 15 is mounted should be thermally isolated from the tube wall. In this modification, the presence of liquid is detected by differentiating the output of the one temperature sensor with respect to time. If the value of the differential exceeds a predetermined threshold, indicating a fall in temperature sufficiently rapid to be due to the consumption of the latent heat of evaporation, it is established that liquid is present and a control signal to that effect may be generated.

The apparatus employing two temperature sensors, however, has the advantage that it is comparatively easy to monitor a difference in two temperatures, and the difference is virtually immune to external influences, which are cancelled out.

The invention may be embodied in other specific forms and manners without departure from the scope thereof. It is preferable, though not essential that the components 15, 16 be mounted adjacent each other. Alternatively, the heater and the associated temperature sensor may be integrated or consist of a single component such as a self-heating thermistor. The cross-sectional shape of the tube 10 is immaterial to the operation of the apparatus and the tube 10 need not be cylindrical.

Thus, the invention provides an apparatus for speedily and reliably detecting the onset of a liquid component in a gas flow. In the context of a heat exchange system, the apparatus may be fitted so as to monitor the fluid flow from the output of an evaporator. The apparatus may then be used as a safety device for generating a warning that liquid is emerging from the evaporator (whether a thermostatic or electronic expansion valve is employed at the evaporator inlet). Alternatively, the apparatus may be used to operate a control regime in which substantially zero superheat is maintained at the evaporator outlet. Furthermore, it is possible to monitor the degree of wetness of the fluid output. The apparatus is not limited to use with any specific control regime.

What is claimed is:

1. A method of sensing the presence of liquid in a flow of gas which is contained by a wall having a thermally conductive portion, the method comprising disposing first and second temperature sensors in thermal contact with respective first and second thermally conductive members in contact with the gas flow and mounted on said wall, the first temperature sensor having a heating means associated therewith, the first thermally conductive member being substantially thermally isolated from said thermally conductive portion of said wall and from the second thermally conductive member and monitoring a difference in the temperatures sensed by the two temperature sensors.

2. A method according to claim 1, wherein the monitoring step comprises detecting a change in said difference which occurs when heat provided by the heating means causes the sensed liquid to vaporise.

3. A method according to claim 2, wherein the monitoring step comprises generating a signal representative of the proportion of liquid present in the gas.

4. A method as claimed in claim 1, in which the gas flow is output from an evaporator of a heat transfer system.

5. A liquid-sensing apparatus for sensing the presence of liquid in a flow of gas which is contained by a wall having a thermally conductive portion, comprising first and second temperature sensors mounted on respective first and second thermally conductive members adapted to be in thermal contact with the gas flow and mounted or mountable on said wall, a heating means arranged to provide heat to the first thermally conductive member and isolating means for thermally isolating the first thermally conductive member from the second thermally conductive member and from said thermally conductive portion of said wall.

6. A liquid-sensing apparatus as claimed in claim 5, further comprising a tube through which, in use, the gas flows, said wall comprising a tube wall of said tube, the first temperature sensor and heating means being mounted on a first portion of the tube wall, the second temperature sensor being mounted on a second portion of the tube wall, and the isolating means thermally isolating said two portions of the tube wall from each other.

7. A liquid-sensing apparatus according to claim 6, wherein said isolating means comprises at least one aperture formed in the tube wall around the first portion.

8. A liquid-sensing apparatus according to claim 7, wherein said at least one aperture comprises a plurality of elongate slots.

9. A liquid-sensing apparatus according to claim 7, wherein said at least one aperture comprises a slot extending substantially completely around the respective portion.

10. A liquid-sensing apparatus according to claim 7, further comprising means for sealing the tube at each said at least one aperture.

11. A liquid-sensing apparatus according to claim 10, wherein said sealing means is a moulding formed around the tube.

12. A liquid-sensing apparatus according to claim 6, wherein said isolating means comprises at least one aperture formed in the tube wall around the second portion.

13. A liquid-sensing apparatus according to claim 8, wherein said at least one aperture comprises a plurality of elongate slots.

14. A liquid-sensing apparatus according to claim 12, wherein said at least one aperture comprises a slot extending substantially completely around the respective portion.

15. A liquid-sensing apparatus according to claim 6, wherein said first and second portions of the tube wall are formed opposing each other.

16. A liquid-sensing apparatus according to claim 6, wherein said first and second portions of the tube wall are formed adjacent each other.

17. A liquid-sensing apparatus according to claim 6, wherein at least one of said first and second portions of the tube wall comprises a substantially rectangular portion of the tube wall.

18. A liquid-sensing apparatus according to claim 6, wherein at least one of said first and second portions is arranged to project into the body of the tube.

19. A liquid-sensing apparatus according to claim 18, wherein the projecting said portion is inclined to face the fluid flow direction through the tube.

20. A liquid-sensing apparatus according to claim 6, wherein said isolating means comprises at least one aperture in the tube wall, separating said first and second portions.

21. A liquid-sensing apparatus as claimed in claim 5, comprising a tube through which, in use, the fluid flows, wherein said first member is thermally isolated from the tube wall.

22. A liquid-sensing apparatus according to claim 21, wherein said second member is thermally isolated from the tube wall.

23. A liquid-sensing apparatus according to claim 22, wherein said first and second members are disposed within a moulding contained within the tube.

24. A liquid-sensing apparatus according to claim 23, wherein the tube is formed in situ around the moulding.

25. A liquid-sensing apparatus according to claim 21, wherein said first and second members are disposed within a moulding contained within the tube.

26. A liquid-sensing apparatus according to claim 25, wherein the tube is formed in situ around the moulding.

27. A liquid-sensing apparatus according to claim 5, wherein the thermally conductive members comprise respective housing members in thermal contact with the respective temperature sensors.

28. A liquid-sensing apparatus according to claim 27, wherein the two housing members are disposed end-to-end with said isolating means comprising a thermally-insulative element sandwiched therebetween.

29. A liquid-sensing apparatus according to claim 27, wherein the housing members comprise a housing within which the temperature sensors and the heating means are disposed and the interior of the housing is sealed from the fluid environment.

30. A liquid-sensing apparatus according to claim 29, wherein the interior of the housing contains gas at substantially atmospheric pressure.

31. A liquid-sensing apparatus according to claim 29, wherein the housing includes a thread adapted for coupling the housing to said wall.

32. A liquid-sensing apparatus according to claim 5, further comprising detection means responsive to change in a difference in the temperatures sensed by the two temperature sensors to generate an output signal representing the presence of liquid in said gas flow.

33. A liquid-sensing apparatus according to claim 32, wherein said detection means is arranged to generate said output signal when the detected change in temperature indicates that a proportion of liquid in the monitored fluid exceeds a predetermined value.

34. A control apparatus for a heat transfer system comprising an evaporator through which fluid is passed while taking up heat from a medium to be cooled using the latent heat of evaporation and valve means for controlling the flow of said fluid as a liquid at the inlet of the evaporator, the control apparatus comprising first sensor means for monitoring said fluid at the outlet of the evaporator, and control means for operating the valve means to adjust the liquid flow in response to an output of said first sensor means, wherein the first sensor means comprises liquid-sensing apparatus as claimed in claim 5.

35. A control apparatus according to claim 34, wherein said control means is adapted to reduce said liquid flow in response to detection of a predetermined proportion of liquid by the liquid-sensing apparatus.

36. A control apparatus system according to claim 35, further comprising second sensor means responsive to the temperature of said medium to be cooled, wherein the control means is operable to control the valve means to adjust said liquid flow in response to the output of the second sensor means when the liquid-sensing apparatus does not detect said predetermined proportion of liquid in said fluid.

37. A heat transfer system including control apparatus as claimed in claim 34.

38. A liquid-sensing apparatus for sensing the presence of liquid in a flow of gas, comprising a tube through which, in use, the gas flows, a first temperature sensor in thermal contact with a first portion of the tube wall, a heating means arranged to provide heat to said first portion, a second temperature sensor in thermal contact with a second portion of the tube wall, and at least one aperture formed in the tube wall between the first and second portions.

39. A liquid-sensing apparatus for sensing the presence of liquid in a flow of gas, comprising a first temperature sensor, a first housing member in thermal contact with the first temperature sensor, a heating means arranged to provide heat to the first housing member, a second temperature sensor and a second housing member in thermal contact with the second temperature sensor, the first and second housing members being disposed end-to-end with a thermally insulative element sandwiched in between so as thermally to isolate said housing members from each other.

40. A liquid-sensing apparatus for sensing the presence of liquid in a flow of gas, comprising first and second temperature sensors mounted on respective first and second thermally conductive members adapted to be in thermal contact with the gas flow, and a heating means arranged to provide heat to said first thermally conductive member, the first and second members being disposed within a thermally insulating moulding such that the first and second members are thermally isolated from each other and the thermally insulating moulding being located within a tube through which, in use, the gas flows, such that the first member is thermally isolated from the tube wall.

* * * * *